United States Patent
Yaginuma et al.

(10) Patent No.: US 8,765,187 B2
(45) Date of Patent: *Jul. 1, 2014

(54) AQUEOUS COMPOSITION

(75) Inventors: Yoshihito Yaginuma, Tokyo (JP); Naoya Yoshida, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 223 days.

This patent is subject to a terminal disclaimer.

(21) Appl. No.: 12/663,961

(22) PCT Filed: Jul. 16, 2008

(86) PCT No.: PCT/JP2008/062853
§ 371 (c)(1),
(2), (4) Date: Dec. 10, 2009

(87) PCT Pub. No.: WO2009/011367
PCT Pub. Date: Jan. 22, 2009

(65) Prior Publication Data
US 2010/0172978 A1 Jul. 8, 2010

(30) Foreign Application Priority Data
Jul. 17, 2007 (JP) .................. 2007-185357

(51) Int. Cl.
*A61K 9/32* (2006.01)
*A61K 47/38* (2006.01)
*A61K 9/14* (2006.01)

(52) U.S. Cl.
USPC ............ 424/495; 424/493; 424/489; 424/464

(58) Field of Classification Search
CPC .. A61K 9/2081; A61K 9/5026; A61K 9/5047
USPC .................. 424/464, 493, 489, 495
See application file for complete search history.

(56) References Cited

U.S. PATENT DOCUMENTS

| | | | |
|---|---|---|---|
| 4,728,513 A | 3/1988 | Ventouras | |
| 4,954,350 A | 9/1990 | Jones et al. | |
| 6,468,561 B1* | 10/2002 | Grillo et al. | 424/480 |
| 7,094,831 B2 | 8/2006 | Kolter et al. | |
| 2004/0131675 A1 | 7/2004 | Yamamoto et al. | |

FOREIGN PATENT DOCUMENTS

| | | |
|---|---|---|
| EP | 1 238 662 A2 | 9/2002 |
| JP | 62-29514 A | 2/1987 |
| JP | 01-502754 | 9/1989 |

(Continued)

OTHER PUBLICATIONS

Dashevsky et al., "Compression of Pellets Coated with Various Aqueous Polymer Dispersions," Int. J. Pharm., vol. 279, p. 19-26, 2004.
International Search Report for PCT/JP2008/062853 mailed Aug. 12, 2008.

(Continued)

*Primary Examiner* — Rachael E Bredefeld
(74) *Attorney, Agent, or Firm* — Greenblum & Bernstein, P.L.C.

(57) ABSTRACT

Disclosed is an aqueous composition containing (a) an ethyl acrylate/methyl methacrylate copolymer or a plasticized vinyl accetate polymer, (b) an ethyl cellulose, (c) a water soluble additive for pharmaceutical products, (d) titanium oxide and (e) water. The solid content mass ratio among the components (a), (b), (c) and (d), namely a:b:c:d is 100:(5-50):(1-50):(0.5-10), and the solid content concentration in the aqueous composition is 0.5-40% by mass.

4 Claims, 5 Drawing Sheets

(56) References Cited

FOREIGN PATENT DOCUMENTS

| | | |
|---|---|---|
| JP | 4-169522 A | 6/1992 |
| JP | 2002-332226 | 11/2002 |
| WO | 88/07369 A1 | 10/1988 |
| WO | 03/000169 A1 | 1/2003 |

OTHER PUBLICATIONS

U.S. Appl. No. 12/675,215 to Yaginuma et al., entitled "Process for Production of Crystalline Cellulose and Tablets Containing Granules" which application is the National Stage of PCT/JP2008/065170, filed Aug. 26, 2008.

Japanese Office Action issued with respect to counterpart Japanese Application No. 2009-523662, dated Mar. 19, 2013.

\* cited by examiner

AQUEOUS COMPOSITION

TECHNICAL FIELD

The present invention relates to an aqueous composition, an aqueous sustained-release film-coating agent for pharmaceutical preparations, sustained-release film-coated granules produced using the same, and a tablet comprising the same.

BACKGROUND ART

Pharmaceutical solid preparations are sometimes coated with a sustained-release film-coating with a view to reducing side effects, reducing the administration frequency, improving the effect of the drug, or the like. The film coating can be applied to a tablet or a granular agent, and often applied to the granular agent in order to reduce the variability of the effects. In particular, in the case of sustained-release film coating, since it is necessary to exhaustively control the dissolution rate of the drug, spherical elementary granules having a uniform particle diameter are often used. Furthermore, since the most preferred dosage form in the pharmaceutical preparations by a patient is a tablet, it is desired that other excipients be added to the film-coated granules to form a tablet.

The general technique for making a tablet is compression with a tableting machine. In order to ensure the practical productivity, manageability and transport properties of tablets, it is necessary to increase tablet hardness by compression with a certain level of pressure. However, often this pressure damages a film of the film-coated granules and impairs the functions thereof. Therefore, attempts to find a solution to the problem by coating with a plurality of films and the like have been made.

It is very advantageous in terms of productivity to finish a film-coating process with one kind of film. One method that allows a film to withstand mechanical stress upon tableting is to provide the film with flexibility like rubber. However, a highly flexible film also has high tackiness on the film surface, and thus agglomeration of granules is likely to occur on film coating. In order to prevent the agglomeration of granules on film coating, while there are coping strategies such as using large granules, reducing the coating rate of the film-coating liquid, and adding a tackiness-reducing agent such as talc to the film-coating liquid, it is conventionally difficult to cope with various sizes of granules without sacrificing the productivity and film properties (drug-dissolution control, mechanical strength).

It is known that a film made from an ethyl acrylate/methyl methacrylate copolymer dispersion and a vinyl acetate polymer dispersion is very flexible. However, the film has high tackiness on the surface, and thus practical film coating has been difficult unless a tackiness-reducing agent such as talc is added. And in particular, the film coating on the granules having an average particle diameter of 300 µm or less has been very difficult.

PATENT DOCUMENT 1 discloses a technology for film-coating granules in the size range of 0.1 to 2 mm with a film-coating agent in which an ethyl cellulose aqueous dispersion and an antistatic agent (talc, light anhydrous silicic acid) are added to an ethyl acrylate/methyl methacrylate copolymer dispersion, mixing the film-coated granules with other excipients, and tableting the mixture. However, in Examples, only examples with spherical granules having a small size of 0.2 to 0.5 mm and a large size of 0.5 to 1.2 mm are shown. Since these granules have an average particle diameter of about 300 µm or more, it can be said that these granules were comparatively easy to be film-coated. Therefore, when small granules having an average particle diameter of 300 µm or less are film-coated with the film-coating agent of the above composition, the agglomeration often occurs for the tackiness of a film base. In addition, the above PATENT DOCUMENT 1 does not show an example relating to tableting and also does not refer anything for the increase in the drug-dissolution rate after tableting.

PATENT DOCUMENT 2 discloses a technology for film-coating granules with a size of 0.5 to 1.5 mm or 0.7 to 1.5 mm with a film-coating agent in which propylene glycol and talc are added to a polyvinyl acetate polymer dispersion. Since these granules also have an average particle diameter of 300 µm or more, these granules were considerably easy to be coated.

NON-PATENT DOCUMENT 1 discloses a technology for film-coating granules having a size of 500 µm or more with a film-coating agent in which triethyl citrate is added to a vinyl acetate polymer dispersion, mixing the film-coated granules with crystalline cellulose, and tableting the mixture. While the film of the above composition has very high tackiness and normally has a problem of the agglomeration of granules, it is considered that the granules could be film-coated since the used granules were large.

PATENT DOCUMENT 1: JP62-029514A
PATENT DOCUMENT 2: U.S. Pat. No. 7,094,831
NON-PATENT DOCUMENT 1: A. Dashevsky, K. Kolter, R. Bodomeier, Compression of pellets coated with various aqueous polymer dispersions, Int. J. Pharm., 2004, vol. 279, p. 19-26

DISCLOSURE OF THE INVENTION

Problems to be Solved by the Invention

An object of the present invention is to provide a low-adherent aqueous composition, which is most suitable for a tablet comprising sustained-release film-coated granules.

Means for Solving the Problems

As the result of intensive studies on prescribing the sustained-release film-coating agent to solve the above problems, the present inventors have found that flexibility and low tackiness can be both satisfied by adding a specified antitackiness agent to the flexible film-coating agent. The present invention has been accomplished thereby.

More specifically, the present invention is as follows.

(1) An aqueous composition comprising (a) an ethyl acrylate/methyl methacrylate copolymer or a plasticized vinyl acetate polymer, (b) an ethyl cellulose, (c) a water-soluble additive for pharmaceutical products, (d) titanium oxide and (e) water, wherein the solid content mass ratio among the components (a), (b), (c) and (d), a:b:c:d, is 100:(5-50):(1-50):(0.5-10), and the solid content concentration in the aqueous composition is 0.5% to 40% by mass.

(2) The aqueous composition according to (1), wherein a cast film of the aqueous composition has a tensile elongation of 150% or more and a tensile strength of 9 N or more.

(3) The aqueous composition according to (1) or (2), wherein the aqueous composition is an aqueous film-coating agent.

(4) The aqueous composition according to (1) or (2), wherein the water-soluble additive for pharmaceutical products is at least one selected from the group consisting of hydroxypropylcellulose, hydroxypropyl methylcellulose, polyvinylpyrrolidone, lactose, sucrose, mannitol, trehalose, and sorbitol.

(5) The aqueous composition according to (4), wherein the aqueous composition is an aqueous film-coating agent.

(6) Film-coated granules comprising elementary granules of an average particle diameter of 300 μm or less comprising crystalline cellulose spherical core particles and a drug, and
a film formed by the aqueous composition according to (3) which is the film-coating agent that coats the elementary granules.

(7) Film-coated granules comprising elementary granules of an average particle diameter of 300 μm or less comprising crystalline cellulose spherical core particles and a drug, and
a film formed by the aqueous composition according to (5) which is the film-coating agent that coats the elementary granules.

(8) A tablet comprising the film-coated granules according to (6).

(9) A tablet comprising the film-coated granules according to (7).

Advantage of the Invention

An advantage of the aqueous composition of the present invention is that sustained-release film-coated granules with less change by tableting can be produced with high productivity.

BRIEF DESCRIPTION OF THE DRAWINGS

FIG. 1 is a dissolution graph of the drug of Example 1
FIG. 2 is a dissolution graph of the drug of Example 2;
FIG. 3 is a dissolution graph of the drug of Example 3;
FIG. 4 is a dissolution graph of the drug of Example 4;
FIG. 5 is a dissolution graph of the drug of Example 5;
FIG. 6 is a dissolution graph of the drug of Example 6;
FIG. 7 is a dissolution graph of the drug of Example 7;
FIG. 8 is a dissolution graph of the drug of Example 8;
FIG. 9 is a dissolution graph of the drug of Comparative Example 2;
and
FIG. 10 is a dissolution graph of the drug of Comparative Example 3.

BEST MODE FOR CARRYING OUT THE INVENTION

Figure 1:
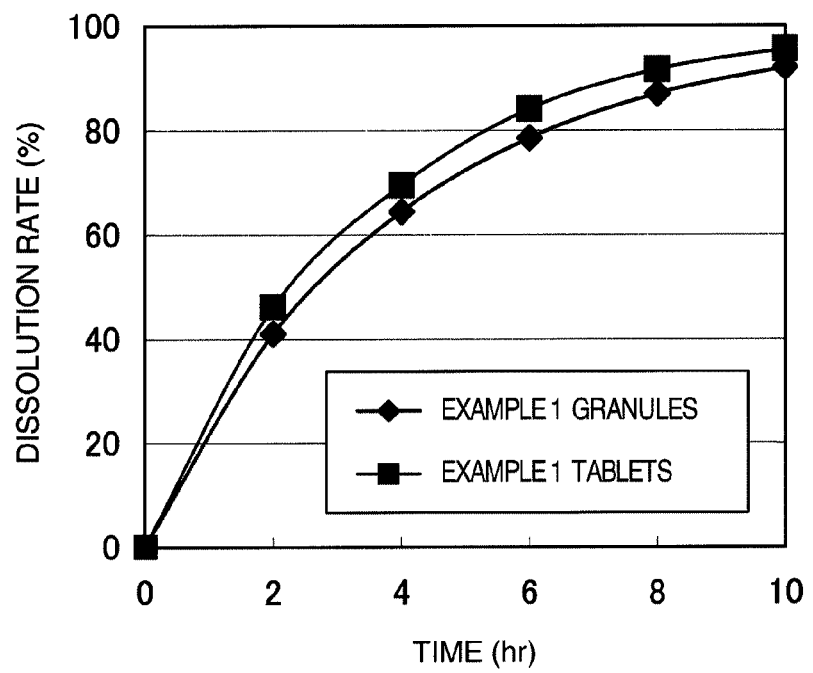
FIGS. 1 to 10 show drug dissolution patterns of film-coated granules-containing tablets obtained by Examples and Comparative Examples.

The present invention will be specifically described below.
The aqueous composition of the present invention comprises an ethyl acrylate/methyl methacrylate copolymer or a plasticized vinyl acetate polymer, an ethyl cellulose, a water-soluble additive for pharmaceutical products, titanium oxide and water, and does not substantially comprise an organic solvent. The aqueous composition is preferably an aqueous film-coating agent.

An ethyl acrylate/methyl methacrylate copolymer is an emulsion of a copolymer resin obtained by polymerizing ethyl acrylate and methyl methacrylate in water using polyoxyethylene nonylphenyl ether as an emulsifier and comprises a small amount of dimethylpolysiloxane. The amount of a solid content is about 30% by mass. Specifically, the ethyl acrylate/methyl methacrylate copolymer meets the standard of "ethyl acrylate/methyl methacrylate copolymer dispersion" in Japanese Pharmaceutical Excipients 2003 (JPE). As commercially available products, Eudragit NE30D (Degussa), Kollicoat EMM30D (BASF) and the like are used.

A plasticized vinyl acetate polymer is obtained by adding a plasticizer (triethyl citrate, propylene glycol, and the like) in about 15% by mass based on the solid content of an aqueous dispersion preferably into vinyl acetate polymer (which is the aqueous dispersion of vinyl acetate resin fine particles (about 27% by mass) comprising 2.5% povidone and 0.3% sodium lauryl sulfate). As commercially available products for vinyl acetate polymer, for example, Kollicoat SR30D (BASF) and the like can be used.

An ethyl cellulose is generally used for film-coating agents for pharmaceutical solid preparations as an aqueous dispersion. As commercially available products, Aquacoat ECD30 (FMC), Surelease (Colorcon), Celioscoat (Asahi Kasei Chemicals Corporation) and the like can be used.

As a water-soluble additive for pharmaceutical products, one or two or more kinds of hydroxypropylcellulose, hydroxypropyl methylcellulose (e.g., trade name "hypromellose"), polyvinylpyrrolidone (e.g., trade name "povidone"), lactose, sucrose, mannitol, trehalose, and sorbitol are used. Drug dissolution pattern of the sustained-release film-coated granules immediately after the production must be appropriate, and the pattern must not greatly change during the storage. To do this, the film is more stable when it is thick, and a film thickness of 10 μm or more is preferable. However, when the amount of film coating is simply increased, the drug dissolution rate is reduced, and in an extreme case, the drug is not dissoluted at all. Accordingly, in order to obtain the targeted film-coating amount (film thickness) and dissolution pattern, the appropriate amount of the water-soluble additive for pharmaceutical products is added.

When the water-solubility of the drug is high, the dissolution rate of the drug is high, and thus the dissolution rate of the drug is reduced by thickening the film. Therefore, when the film is thickened, the need for adding the water-soluble additive for pharmaceutical products is less. However, in the case of long-time sustained-release preparations, 100% of the drug is often not dissoluted unless the water-soluble additive for pharmaceutical products is not added. In that case, the addition of the additive for water-soluble pharmaceutical products is necessary. Since hypromellose or mannitol has a property to reduce the tackiness of the film, its use is particularly preferable.

Titanium oxide refers to titanium dioxide ($TiO_2$) and meets the standard of "titanium oxide" in the Japanese Pharmacopoeia, Fifteenth Edition (hereinafter, JP). In addition, accessory components such as a plasticizer may be contained.

The aqueous composition, preferably a film-coating liquid is prepared, for example, by procedures of (1) adding ethyl cellulose to pure water while stirring with a propeller, and stirring the mixture for about 10 minutes, (2) further adding hypromellose and titanium oxide thereto while continuing stirring, and stirring the mixture for about 15 minutes, (3) further adding an ethyl acrylate/methyl methacrylate copolymer (or a mixture solution obtained by previously mixing a plasticizer and vinyl acetate polymer) thereto, and gently stirring for about 10 minutes, and (4) screening the resulting mixture with a sieve opening of 250 μm.

The composition of the aqueous composition, preferably the film-coating liquid is (a) an ethyl acrylate/methyl methacrylate copolymer or a plasticized vinyl acetate polymer, (b) an ethyl cellulose, (c) a water-soluble additive for pharmaceutical products and (d) titanium oxide, wherein the solid content weight ratio a:b:c:d is appropriately 100:5-50:1-50:0.5-10, more preferably 100:5-25:1-50:2-8, and further preferably 100:5-25:1-50:3-7. The solid content concentration in the film-coating liquid is appropriately 0.5% to 40% by mass, more preferably 5% to 35% by mass, and further preferably 10% to 30% by mass. As described above, a film formed from an ethyl acrylate/methyl methacrylate copolymer dispersion or a plasticized vinyl acetate polymer dispersion has very high flexibility. By adding an ethyl cellulose aqueous dispersion and titanium oxide thereto, tackiness can be reduced and strength can be improved while maintaining flexibility.

Flexibility and strength are each represented by a tensile elongation and a tensile strength of a cast film set forth below (Examples), and the tensile elongation of 150% or more and the tensile strength of 9 N or more are preferable. When the tensile elongation is 150% or more and the tensile strength is 9 N or more, the film is not damaged by mechanical stress upon tableting, and also, the dissolution rate of the drug does not change. The tensile elongation is more preferably 200% to 800%, and further preferably 300% to 800%. Also, the tensile strength is more preferably 10 N to 300 N, and further preferably 11 N to 300 N. Tackiness is also a physical property determined by a method set forth below (Examples), the evaluation result of tackiness is preferably "1: None" in the evaluation standard set forth below. In order to obtain the above physical properties, the solid content weight ratio of the film-coating liquid components is fine-tuned as needed.

While the ethyl cellulose aqueous dispersion does not form a film without a plasticizer, it acts as a tackiness-reducing agent with very high suspension stability in the present invention. In addition, while talc is generally used for the purpose of reducing tackiness, in this formulation, titanium oxide exhibits highly excellent properties in terms of tackiness reduction, strength improvement, and operability improvement on the film coating (reduction of the adhesion amount to the inner side of an apparatus by static electricity). Incidentally, examples using titanium oxide for this purpose are not found.

The composition of the aqueous composition of the invention of the present application, preferably the film-coating liquid is film-coated to elementary granules (drug-containing particles) with a known method. The elementary granules may be granules prepared by high-speed stirring granulation, fluidized-bed granulation, extrusion granulation, extrusion/spheronization granulation method, or drug layering method using core particles, or drug crystalline particles. However, in order to make sustained-release film-coated granules of which dissolution rate is to be exhaustively controlled, spherical granules prepared using the layering method is the best. The size of the elementary granules may be determined depending on the formulation design, and smaller elementary granules are desired for tableting. It is because of suppression of damage on the film by mechanical stress upon tableting, and also because it is effective for suppressing segregation (variation of the ratio of mixing components) upon mixing and transporting powders for tableting and upon tableting. Specifically, the elementary granules have an average particle diameter of preferably 300 μm or less, and further preferably 200 μm or less. The average particle diameter herein refers to a value of 50% by mass cumulated in the cumulative distribution under sieve of particle diameters determined by a sieving method.

The core particles used in the drug layering method are pharmaceutically inert, more specifically, do not contain a drug, and comprise crystalline cellulose, lactose, sucrose, mannitol, corn starch, powdered cellulose, calcium hydrogen phosphate, calcium carbonate, low-substituted hydroxypropylcellulose, carmellose calcium, partially pregelatinized starch, croscarmellose sodium, crospovidone, and carboxymethyl starch, hydroxypropylcellulose, povidone or xanthan gum, and the like. Among them, the crystalline cellulose spherical core particles are preferably used since the agglomeration of granules are less on the layering. In particular, it is difficult to perform drug layering on core particles having an average particle diameter of 300 μm or less without agglomeration, and the crystalline cellulose spherical core particles are preferably used also from that point. As examples of the crystalline cellulose spherical core particles, CELPHERE (registered trademark, Asahi Kasei Chemicals Corporation) can be included.

The method for producing elementary granules according to the drug layering method using core particles are described below. Layering methods, on the core particles, include a method for coating by concurrently providing drug powder and aqueous binder solution, a method for coating by providing suspension of drug particles, a method for coating by providing aqueous drug solution, and the like. In the case of the method for coating by concurrently providing drug powder and aqueous binder solution, an additive other than drug, for example, an excipient is used mixed with drug powder as needed. When a drug suspension or aqueous solution is used, a fluidized-bed coating apparatus (sometimes referred to as fluidized-bed drier or fluidized-bed granulating machine) is suitably used.

As the fluidized-bed coating apparatus, not only an ordinarily fluidized-bed type, but also a spouted bed type having a guide tube (Wurster column) inside thereof, a tumbling fluidized bed type equipped with a rotation mechanism on the bottom thereof and the like can be used. Examples of apparatuses can include "Flow Coater" (trade name) and "Spiral Flow" (trade name) manufactured by Freund Corporation, "WST/WSG Series" and "GPCG Series" manufactured by Glatt GmbH, "New Marumerizer" (trade name) manufactured by Fuji Paudal Co., Ltd., "Multiplex" (trade name) manufactured by Powrex Corporation, and the like. The layering liquid can be supplied by selecting a method suited for each of apparatuses from top spray, bottom spray, side spray and tangential spray, and spraying to the core particles continuously or intermittently. The above apparatuses are preferably used since even smaller core particles can be produced with less agglomeration.

The elementary granules normally comprise at least 0.01% by mass of a drug. The drug as used in the present invention refers to the one used for treatment, prevention or diagnosis of human or animal diseases but the one is not an instrument or a machine. Examples include anti-epileptic agents (such as phenytoin, acetylpheneturide, trimethadione, phenobarbital, primidone, nitrazepam, sodium valproate, and sultiame), antipyretic, analgesic and anti-inflammatory agents (such as acetaminophen, phenyl acetylglycine methyl amide, mefenamic acid, diclofenac sodium, floctafenine, aspirin, aspirin aluminum, ethenzamide, oxyphenbutazone, sulpyrin, phenylbutazone, ibuprofen, alclofenac, naproxen, ketoprofen, tinoridine hydrochloride, benzydamine hydrochloride, tiaramide hydrochloride, indomethacin, piroxicam, and salicylamide), antivertigo agents, for example, dimenhydrinate, meclizine hydrochloride, and difenidol hydrochloride), narcotics (such as opium alkaloids hydrochlorides, morphine hydrochloride, codeine phosphate, dihydrocodeine phosphate, and oxymethebanol), agents for psychological use (such as chlorpromazine hydrochloride, levomepromazine maleate, perazine maleate, propericiazine, perphenazine, chlorprothixene, haloperidol, diazepam, oxazepam, oxazolam, mexazolam, alprazolam, and zotepine), skeletal muscle relaxants (such as chlorzoxazone, chlorphenesin carbamate, chlormezanone, pridinol mesylate, and eperisone hydrochloride), autonomic nerve agents (such as betanecol chloride, neostigmine bromide, and pyridostigmine bromide), antispasmodic agents (such as atropine sulfate, butropium bromide, butylscopolamine bromide, propantheline bromide, and papaverine hydrochloride), antiparkinsonian agents (such as biperiden hydrochloride, trihexyphenidyl hydrochloride, amantadine hydrochloride, and levodopa), antihistaminic agents (such as diphenhydramine hydrochloride, dl-chlorpheniramine maleate, promethazine, mequitazine, and clemastine fumarate), cardiotonic agents (such as aminophylline, caffeine, dl-isoproterenol hydrochloride, etilefrin hydrochloride, norfenerine hydrochloride, and ubidecarenone), antiarrhythmic agents (such as procainamide hydrochloride, pindolol, metoprolol tartrate, and disopyramide), diuretics (such as potassium chloride, cyclopenthiazide, hydrochlorothiazide, triamterene, acetazolamide, and furosemide), antihypertensive agents (such as hexamethonium bromide, hydralazine hydrochloride, syrosingopine, reserpine, propranolol hydrochloride, captopril, and methyldopa), vasoconstrictor agents (such as dihydroergotamine mesylate), vasodilatory agents (such as etafenone hydrochloride, diltiazem hydrochloride, carbochromen hydrochloride, pentaerythritol tetranitrate, dipyridamole, isosorbide nitrate, nifedipine, nicametate citrate, cyclandelate, and cinnarizine), agents for arteriosclerosis (such as ethyl linoleate, lecithin, and clofibrate), agents for the circulatory organs (such as nicardipine hydrochloride, meclofenoxate hydrochloride, cytochrome C, pyridinol carbamate, vinpocetine, calcium hopantenate, pentoxifylline, and idebenone), respiratory stimulants (such as dimefline hydrochloride), antitussives and expectorants (such as codeine phosphate, dihydrocodeine phosphate, dextromethorphan hydrobromide, noscapine, methyl L-cysteine hydrochloride, bromhexine hydrochloride, theophylline, ephedrine hydrochloride, and amlexanox), cholagogues (such as osalmid, phenyl propanol, and hymecromone), agents for intestinal disorders (such as berberine chloride, and loperamide hydrochloride), agents for digestive organs (such as metoclopramide, fenipentol, and domperidone), vitamin preparations (such as retinol acetate, dihydrotachysterol, etretinate, thiamine hydrochloride, thiamine nitrate, fursultiamine, octotiamine, cycotiamine, riboflavin, pyridoxine hydrochloride, pyridoxal phosphate, nicotinic acid, pantethine, cyanocobalamin, biotin, ascorbic acid, phytonadione, and menatetrenone), antibiotics (such as benzathine benzylpenicillin, amoxicillin, ampicillin, cyclacillin, cefaclor, cephalexin, cefuroxime axetil, erythromycin, kitasamycin, josamycin, chloramphenicol, tetracycline, griseofulvin, and cefuzonam sodium), and chemotherapeutic agents (such as sulfamethoxazole, isoniazid, ethionamide, thiazosulfone, nitrofurantoin, enoxacin, ofloxacin, and norfloxacin).

The elementary granules are subjected to film coating using the same apparatus as in the drug layering method. As the fluidized-bed coating apparatuses, a spouted bed type having a guide tube (Wurster column) inside thereof and a tumbling fluidized bed type equipped with a rotation mechanism on the bottom thereof are preferably used. A film-coating liquid can be supplied by selecting a method suited for each of apparatuses from top spray, bottom spray, side spray and tangential spray, and spraying to the elementary particles. During spraying, the film-coating liquid is constantly stirred with a propeller and the like, so as not to precipitate titanium oxide in the film-coating liquid. After completion of spraying, the resulting film-coated granules are dried as they are or after controlling the air flow and temperature as needed, without taking out the samples from the apparatus. It is preferable to further carry out heat treatment (curing) since film-forming property is increased.

The resulting film-coated granules from which agglomerated granules (coarse particles) are removed with a sieve and the like are encapsulated separately or concurrently with other film-coated granules or concurrently with other additive powders for pharmaceutical products. Alternatively, the film-coated granules are mixed with other additive powders for pharmaceutical products, tableted, and formed into a tablet. As powders for tableting, those having high compression compactibility and disintegrating property, which do not cause damage to the film-coated granules as possible, are desired. Examples having high compression compactibility include crystalline cellulose. Addition of a disintegrant is also effective. Tableting is performed with a rotary tableting machine, and a forced feeder is preferably used from the viewpoint of prevention of segregation. While the higher content of the film-coated granules in the tablet is desired, the content is in the range of 1% to 70% by mass from the balance of compactibility and disintegrating property, and practically in the range of 10% to 50% by mass. When an appropriate powder for tableting is selected, it is possible to be used as an orally-disintegrating tablet.

It is preferable that the aqueous composition of the present invention, preferably the aqueous film-coating agent, can obtain the above film-coated granules with high productivity.

In addition, it is preferable that the aqueous composition of the present invention, preferably the aqueous film-coating agent, has the property that the drug dissolution rates of the above film-coated granules and the above tablet are equivalent.

EXAMPLES

The present invention will be described based on examples. First, the determination methods of physical properties are collectively described below.

<Tackiness, Tensile Elongation and Tensile Strength of Cast Film>

(1) A film-coating liquid is poured in a plastic petri dish having a diameter of 8.5 cm in an appropriate amount (so as to have a thickness of cast film of 0.27 to 0.37 mm. When the concentration is 17%, the amount is 11.3 g or so.).

(2) The sample in the petri dish is dried at 40° C. in an oven without air circulation for 10 hours.

(3) Immediately after taking out the dried sample from the oven, tackiness (stickiness) is evaluated by touching the film surface with a fingertip (previously washed well with soap and dried enough). The evaluation standard of tackiness (4-grade evaluation) and qualitative coating property corresponding thereto are as described below.

1 None: Spraying is possible at a comparatively high rate (minor agglomeration), 2 Minor: Coating is possible when reducing the spray rate (some agglomeration), 3 Weak: Coating is barely possible with an intermittent spray (much agglomeration), and 4 Strong: Agglomeration is observed at once and coating is not possible.

(4) The petri dish is further heat-treated at 80° C. in an oven without air circulation for 1 hour.

(5) The heat-treated product is cooled to room temperature, and thereafter the film is peeled off and cut out into a rectangle of 10 mm×30 mm.

(6) The cast film is set on a tensile tester (creep meter, RE-33005 (adaptor for a sheet tensile test, using a 200 N load cell), Yamaden Co., Ltd.) so as to have a spacing of measurement points of the tensile test of 10 mm and pulled the film at a rate of 0.5 mm/s. Elongation (mm) and strength (tensile strength) [N] on breaking the film are obtained.

(7) Tensile elongation [%] (=100×Elongation/10) is calculated.

<Average Particle Diameters [μm] of Film-Coated Granules, Elementary Granules, Core Particles>

Particle size distribution is determined with a Ro-Tap sieve shaker (Sieve Shaker Type A, manufactured by Hirako Seisaku-sho Co., Ltd.) by screening 10 g of the sample using a JIS standard sieve for 15 minutes. The particle diameter of 50% by mass cumulated in the cumulative distribution under sieve is defined as an average particle diameter.

<Collection Ratio [%] of Elementary Granules and Film-Coated Granules>

The collection ratio is determined by dividing the collection amount of elementary granules or film-coated granules by the total amount of raw materials employed and is represented as % by mass.

<Agglomeration Ratio [%] of Elementary Granules and Film-Coated Granules>

Agglomerated products (coarse particles) of elementary granules obtained by layering or film-coated granules obtained by film coating are removed with a sieve. The weight is divided by the total amount and represented as % by mass.

<Dissolution Test of Drug>

The dissolution test is carried out in accordance with "Dissolution Test" in General Tests of JP. "Apparatus 2" (paddle method) is used as an apparatus with a rotation speed of a paddle at 100 rpm, and "1st fluid for dissolution test" of the Pharmacopeia is used as a dissolution medium.

Example 1

Crystalline cellulose spherical core particles (C1) (having an average particle diameter of 237 μm, not comprising particles having a particle diameter of 355 μm or more) were charged in a tumbling fluidized bed type coating apparatus and were sprayed and coated (layered) with an aqueous drug dispersion (3.85% riboflavin, 1.15% povidone), to give elementary granules (G1). The resulting elementary granules (G1) comprised riboflavin in an amount of 1.95% by mass (2% by mass based on core particles) and had an average particle size of 238 μm. The layering conditions were described as below.
(1) Apparatus Used: Multiplex (trade name) MP-25 (Powrex Corporation)
(2) Air Flow: 8 m³/min
(3) Charge-Air Temperature: 70° to 75° C.
(4) Exhaust-Air Temperature: 37° to 39° C.
(5) Rotation Speed of Roter: 250 to 300 ppm
(6) Amount of Core Particles: 18 kg
(7) Amount of Aqueous Drug Dispersion: 9.345 kg
(8) Spray Rate of Aqueous Drug Dispersion: 100 to 110 g/min
(9) Spray Air Pressure: 0.55 MPa
(10) Spray Air Flow: 702 NL/min Subsequently, in accordance with the method described above, a film-coating liquid (solid content concentration of 17% by mass) (L1) comprising (a) an ethyl acrylate/methyl methacrylate copolymer, (b) an ethyl cellulose, (c) hypromellose and (d) titanium oxide was prepared. Eudragit NE30D (Degussa) as the ethyl acrylate/methyl methacrylate copolymer, Aquacoat ECD30 (FMC) as the ethyl cellulose, TC-5(E) (Shin-Etsu Chemical Co., Ltd.) as hypromellose, and NA61 (Toho Titanium Co., Ltd.) as titanium oxide were used. The solid content mass ratio was made as a:b:c:d=70:7.5: 20:0.5 (=100:10.7:28.6:3.6). The cast film had the tensile elongation of 396% and the tensile strength of 19.8 N, and the tackiness was "1: None".

Next, elementary particles (G1) were charged in the tumbling fluidized bed type coating apparatus and were sprayed and coated (film-coated) with the film-coating liquid (L1), and particles having a particle diameter of 355 μm or more were removed with a sieve, to give film-coated granules (F1). The resulting film-coated granules (F1) had the film-coating amount of 20% by mass (based on elementary granules (G1)), and the average particle diameter of 271 μm (the film thickness was about 16.5 μm). The collection ratio was 99.9%, and the agglomeration ratio was 5.7% (355 μm or more). The dissolution rates of riboflavin were 41.0% at 2 hours, 64.4% at 4 hours, 78.5% at 6 hours, 87.0% at 8 hours, and 92.0% at 10 hours. The film-coating conditions were described as below.
(1) Apparatus Used: Multiplex (trade name) MP-25 (Powrex Corporation)
(2) Air Flow: 7.5 to 8 m³/min
(3) Charge-Air Temperature: 45° to 50° C.
(4) Exhaust-Air Temperature: 27° to 31° C.
(5) Rotation Speed of Roter: 240 to 300 ppm
(6) Amount of Core Particles: 10 kg
(7) Amount of Film-Coating Liquid: 11.7 kg
(8) Spray Rate of Film-Coating Liquid: 100 to 120 g/min
(9) Spray Air Pressure: 0.6 MPa
(10) Spray Air Flow: 702 NL/min Lastly, 50% by mass of the film-coated granules (F1), 40% by mass of crystalline cellulose (CEOLUS PH-200 (trade name), Asahi Kasei Chemicals Corporation), 10% by mass of partly pregelatinized starch (PCS PC-10, Asahi Kasei Chemicals Corporation) were mixed together and tableted with a rotary tableting machine (Clean Press Correct 12HUK (trade name), Kikusui Seisakusho, Ltd.). As die/punch for tableting, 12 sets of die/punch having a diameter of 8 mm and a punch concave curve radius of 12 mm were used. Tableting was carried out at a rotation speed of the turntable of 15 rpm and a compression pressure of 5.1 kN, to give a 250 mg tablet.

The resulting tablets had the hardness of 70 N, the disintegration time of 73 s, and the tablet weight variation of 0.4%. The dissolution rates of riboflavin were 46.2% at 2 hours, 69.5% at 4 hours, 84.1% at 6 hours, 91.6% at 8 hours, and 95.5% at 10 hours. Namely, sustained-release film-coated granules-containing tablets which were excellent in hardness and disintegrating property with less weight variation and had nearly-unchanged drug dissolution patterns as compared to the film-coated granules before tableting could be obtained. The drug dissolution pattern is shown in FIG. 1.

Example 2

The same procedures as in Example 1 were carried out, to prepare a film-coating liquid (solid content concentration of 17% by mass) (L2) with the solid content mass ratio of the formulation components of a:b:c:d=72:7.5: 20:0.5 (=100:10.7:28.6:0.7). The cast film had the tensile elongation of 435% and the tensile strength of 22.5 N, and the tackiness was "1: None".

Next, the same procedures as in Example 1 were carried out except using (L2) as the film-coating liquid, to give film-coated granules (F2). The resulting film-coated granules (F2) had the film-coated amount of 20% by mass (based on elementary granules (G1)), and the average particle diameter of 270 μm (the film thickness was about 16.0 μm). The collection ratio was 90.8%, and the agglomeration ratio was 7.2% (355 μm or more). The dissolution rates of riboflavin were 41.5% at 2 hours, 65.2% at 4 hours, 79.5% at 6 hours, 88.5% at 8 hours, and 93.0% at 10 hours.

Figure 2:
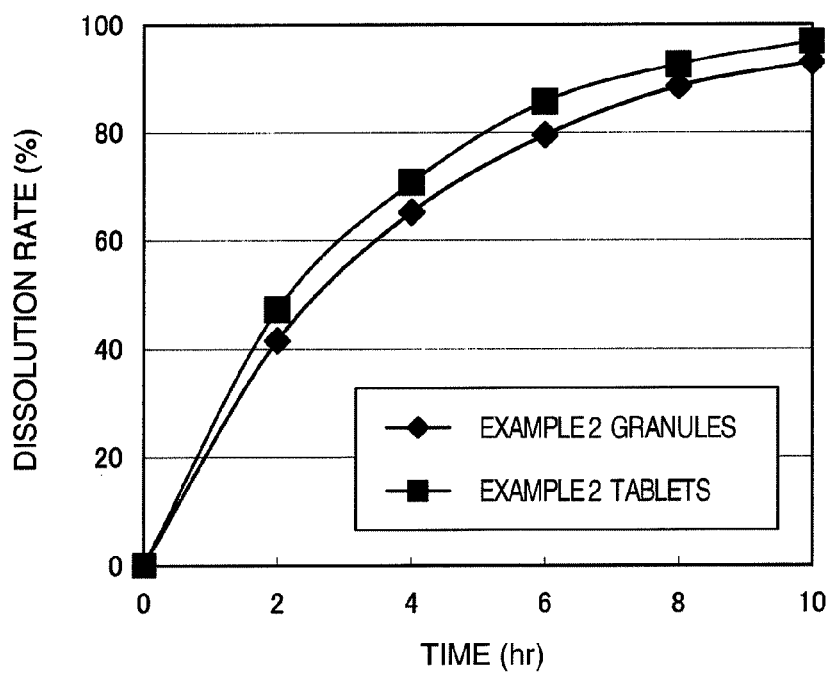

Lastly, the same procedures as in Example 1 were carried out except using (F2) as the film-coated granules, to give tablets comprising the film-coated granules in 50% by mass. The resulting tablets had the hardness of 75 N, the disintegration time of 80 s, and the tablet weight variation of 0.7%. The dissolution rates of riboflavin were 47.2% at 2 hours, 70.7% at 4 hours, 85.7% at 6 hours, 92.6% at 8 hours, and 96.8% at 10 hours. Namely, sustained-release film-coated granules-containing tablets which were excellent in hardness and disintegrating property with less weight variation and had nearly-unchanged drug dissolution patterns as compared to the film-coated granules before tableting could be obtained. The drug dissolution pattern is shown in FIG. 2.

Example 3

In accordance with the method described above, a film-coating liquid (solid content concentration of 17% by mass) (L3) comprising (a) a plasticized vinyl acetate polymer, (b) an ethyl cellulose, (c) hypromellose and (d) titanium oxide was prepared. The mixture of Kollicoat SR30D (BASF) and triethyl citrate (15% by mass based on the solid content of Kollicoat SR30D) was used as the plasticized vinyl acetate polymer. Aquacoat ECD30 (FMC) as the ethyl cellulose, TC-5(E)(trade name, Shin-Etsu Chemical Co., Ltd.) as hypromellose, and NA61 (Toho Titanium Co., Ltd.) as titanium oxide were used. The solid content weight ratio of the above components was made as a:b:c:d=65:13:16:6 (=100:20:24.6:9.2). The cast film had the tensile elongation of 540% and the tensile strength of 12.5 N, and the tackiness was "1: None".

Next, the same procedures as in Example 1 were carried out except using (L3) as the film-coating liquid, to give film-coated granules (F3). The resulting film-coated granules (F3) had the film-coated amount of 20% by mass (based on elementary granules (G1)), and the average particle diameter of 272 μm (the film thickness was about 17.0 μm). The collection ratio was 98.8%, and the agglomeration ratio was 4.3% (355 μm or more). The dissolution rates of riboflavin were 45.6% at 2 hours, 60.9% at 4 hours, 73.4% at 6 hours, 80.7% at 8 hours, and 84.9% at 10 hours.

Figure 3:
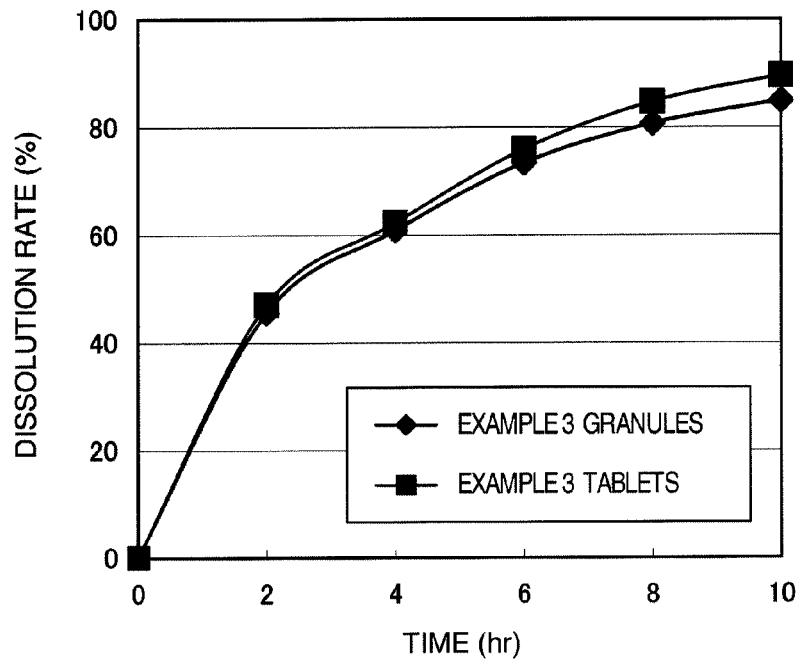

Lastly, the same procedures as in Example 1 were carried out except using (F3) as the film-coated granules, to give tablets comprising the film-coated granules in 50% by mass. The resulting tablets had the hardness of 90 N, the disintegration time of 95 s, and the tablet weight variation of 0.8%. The dissolution rates of riboflavin were 47.1% at 2 hours, 62.3% at 4 hours, 76.0% at 6 hours, 84.7% at 8 hours, and 89.6% at 10 hours. Namely, sustained-release film-coated granules-containing tablets which were excellent in hardness and disintegrating property with less weight variation and had nearly-unchanged drug dissolution patterns as compared to the film-coated granules before tableting could be obtained. The drug dissolution pattern is shown in FIG. 3.

Example 4

According to Example 1 except using crystalline cellulose spherical core particles (C2) (having an average particle diameter of 395 μm, not comprising particles having a particle diameter of 500 μm or more), elementary granules (G2) were obtained.

Further, according to Example 1, film-coating granules (F4) were obtained. The resulting film-coated granules (F4) had the film-coated amount of 20% by mass (based on elementary granules (G2)), and the average particle size of 412 μm. The collection ratio was 99.6%, and the agglomeration ratio was 4.3% (500 μm or more). The dissolution rates of riboflavin were 27.1% at 2 hours, 49.8% at 4 hours, 65.0% at 6 hours, 74.8% at 8 hours, and 81.2% at 10 hours.

Figure 4:
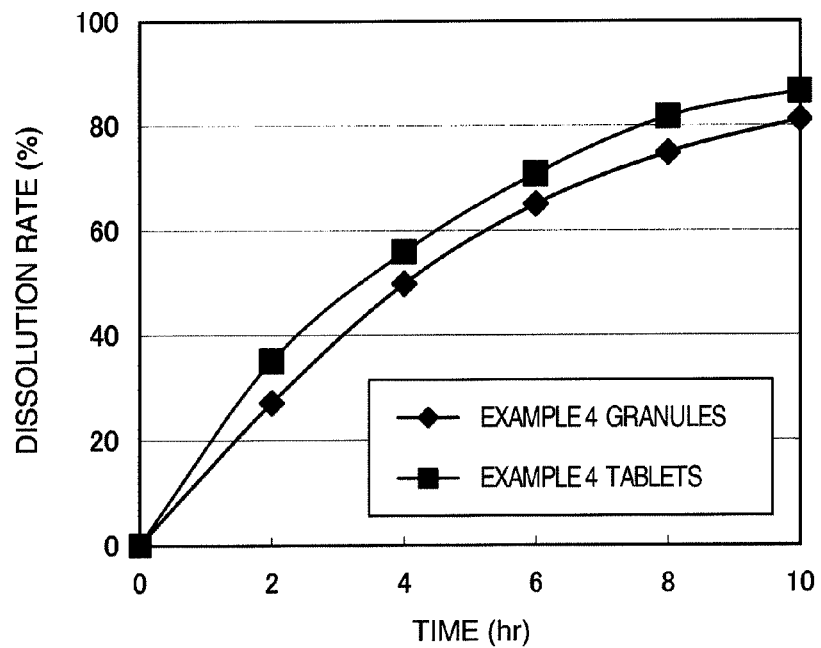

Lastly, the same procedures as in Example 1 were carried out except using the film-coated granules (F4), to give tablets comprising the film-coated granules in 50% by mass. The resulting tablets had the hardness of 64 N, the disintegration time of 51 s, and the tablet weight variation of 1.4%. The dissolution rates of riboflavin were 35.1% at 2 hours, 55.8% at 4 hours, 70.8% at 6 hours, 81.7% at 8 hours, and 86.6% at 10 hours. Namely, sustained-release film-coated granules-containing tablets which were excellent in hardness and disintegrating property with less weight variation and had nearly-unchanged drug dissolution patterns as compared to the film-coated granules before tableting could be obtained. The drug dissolution pattern is shown in FIG. 4.

Example 5

The same procedures as in Example 1 were carried out, to prepare a film-coating liquid (solid content concentration of 17% by mass) (L4) with the solid content mass ratio of the formulation components of a:b:c:d=56.4:27.1:16:0.5 (=100:48:28.6:0.8). The cast film had the tensile elongation of 198% and the tensile strength of 12.5 N, and the tackiness was "1: None".

Next, the same procedures as in Example 1 were carried out except using (L4) as the film-coating liquid, to give the film-coated granules (F5). The resulting film-coated granules (F5) had the film-coated amount of 20% by mass (based on elementary granules (G1)), and the average particle diameter of 272 μm (the film thickness was about 17.0 μm). The collection ratio was 98.5%, and the agglomeration ratio was 3.8% (355 μm or more). The dissolution rates of riboflavin were 47.6% at 2 hours, 69.7% at 4 hours, 85.3% at 6 hours, 92.3% at 8 hours, and 96.7% at 10 hours.

Figure 5:
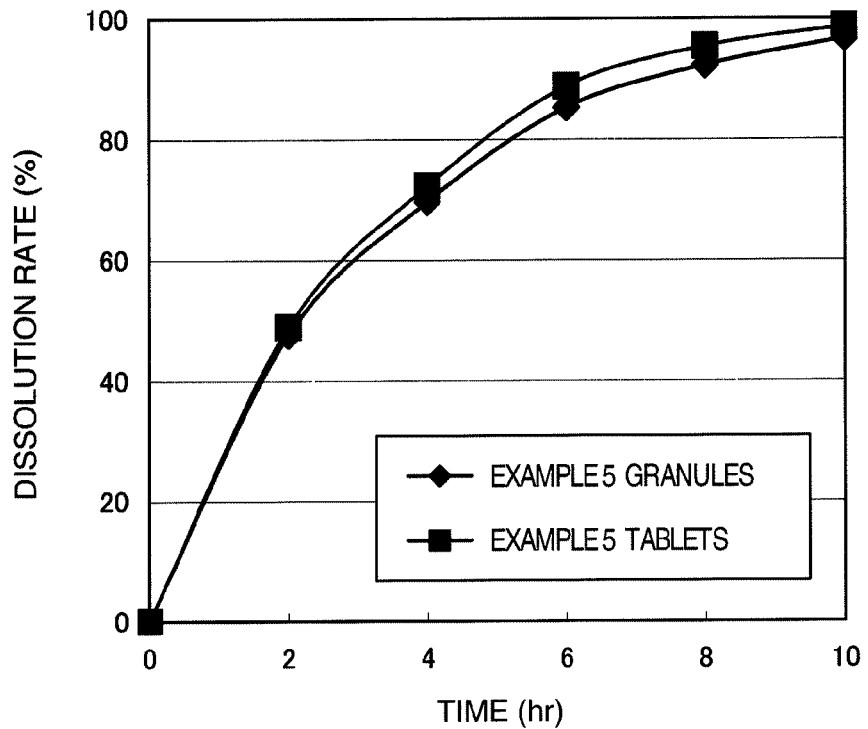

Lastly, the same procedures as in Example 1 were carried out except using (F5) as the film-coated granules, to give tablets comprising the film-coated granules in 50% by mass. The resulting tablets had the hardness of 72 N, the disintegration time of 75 s, and the tablet weight variation of 0.5%. The dissolution rates of riboflavin were 48.9% at 2 hours, 72.3% at 4 hours, 88.8% at 6 hours, 95.4% at 8 hours, and 98.8% at 10 hours. Namely, sustained-release film-coated granules-containing tablets which were excellent in hardness and disintegrating property with less weight variation and had nearly-unchanged drug dissolution patterns as compared to the film-coated granules before tableting could be obtained. The drug dissolution pattern is shown in FIG. 5.

Example 6

The same procedures as in Example 1 were carried out, to prepare a film-coating liquid (solid content concentration of 17% by mass) (L5) with the solid content mass ratio of the formulation components of a:b:c:d=68.9:4.8:19.7:6.6 (=100:7:28.6:9.5). The cast film had the tensile elongation of 580% and the tensile strength of 18.9 N, and the tackiness was "1: None".

Next, the same procedures as in Example 1 were carried out except using (L5) as the film-coating liquid, to give film-coated granules (F6). The resulting film-coated granules (F6) had the film-coated amount of 20% by mass (based on elementary granules (G1)), and the average particle diameter of 275 μm (the film thickness was about 18.5 μm). The collection ratio was 91.6%, and the agglomeration ratio was 6.0% (355 μm or more). The dissolution rates of riboflavin were 41.2% at 2 hours, 56.6% at 4 hours, 70.1% at 6 hours, 77.6% at 8 hours, and 83.3% at 10 hours.

Figure 6:
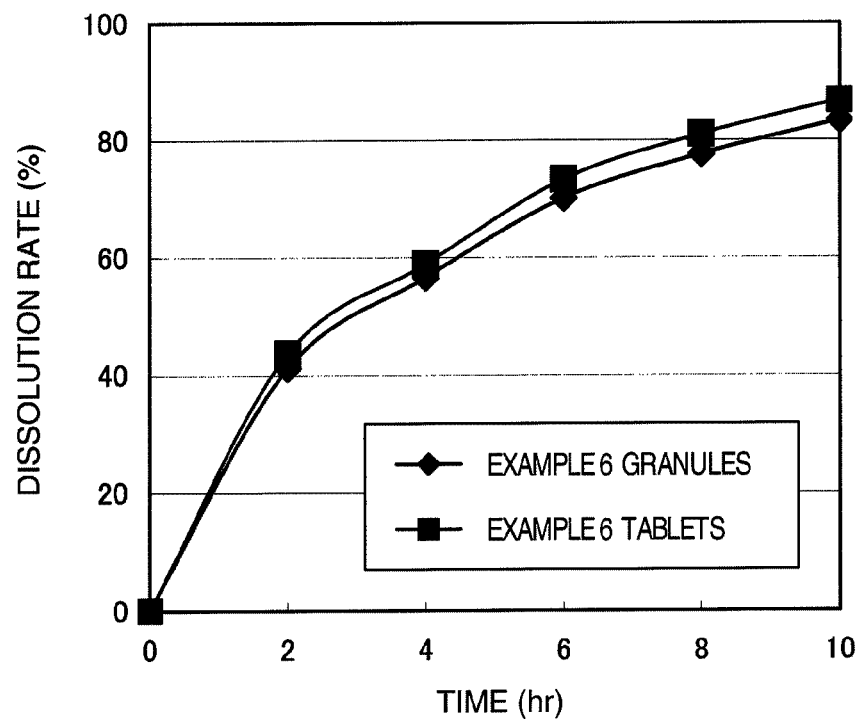

Lastly, the same procedures as in Example 1 were carried out except using (F6) as the film-coated granules, to give tablets comprising the film-coated granules in 50% by mass. The resulting tablets had the hardness of 77 N, the disintegration time of 85 s, and the tablet weight variation of 0.9%. The dissolution rates of riboflavin were 43.7% at 2 hours, 58.9% at 4 hours, 73.3% at 6 hours, 81.0% at 8 hours, and 86.0% at 10 hours. Namely, sustained-release film-coated granules-containing tablets which were excellent in hardness and disintegrating property with less weight variation and had nearly-unchanged drug dissolution patterns as compared to the film-coated granules before tableting could be obtained. The drug dissolution pattern is shown in FIG. 6.

Example 7

The same procedures as in Example 1 were carried out, to prepare a film-coating liquid (solid content concentration of 17% by mass) (L6) with the solid content mass ratio of the formulation components of a:b:c:d=68.6:7.3:19.6:4.5 (=100:10.7:28.6:6.5). The cast film had the tensile elongation of 235% and the tensile strength of 12.1 N, and the tackiness was "1: None".

Next, the same procedures as in Example 1 were carried out except using (L6) as the film-coating liquid, to give film-coated granules (F7). The resulting film-coated granules (F7) had the film-coated amount of 20% by mass (based on elementary granules (G1)), and the average particle diameter of 274 μm (the film thickness was about 18.0 m). The collection ratio was 99.9%, and the agglomeration ratio was 4.1% (355 μm or more). The dissolution rates of riboflavin were 39.2% at 2 hours, 63.5% at 4 hours, 76.5% at 6 hours, 84.9% at 8 hours, and 90.2% at 10 hours.

Figure 7:
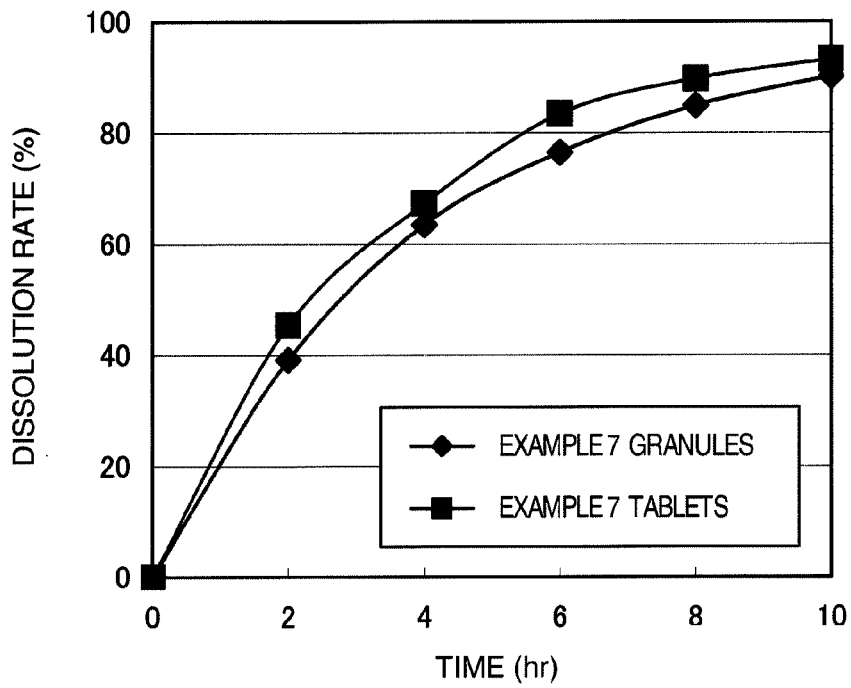

Lastly, the same procedures as in Example 1 were carried out except using (F7) as the film-coated granules, to give tablets comprising the film-coated granules in 50% by mass. The resulting tablet had the hardness of 76 N, the disintegration time of 71 s, and the tablet weight variation of 0.7%. The dissolution rates of riboflavin were 45.4% at 2 hours, 67.3% at 4 hours, 83.4% at 6 hours, 89.7% at 8 hours, and 93.2% at 10 hours. Namely, sustained-release film-coated granules-containing tablets which were excellent in hardness and disintegrating property with less weight variation and had nearly-unchanged drug dissolution patterns as compared to the film-coated granules before tableting could be obtained. The drug dissolution pattern is shown in FIG. 7.

Example 8

The same procedures as in Example 1 were carried out, to prepare a film-coating liquid (solid content concentration of 17% by mass) (L7) with the solid content mass ratio of the formulation components of a:b:c:d=62.8:6.7:28.2:2.3 (=100:10.7:45:3.6). The cast film had the tensile elongation of 278% and the tensile strength of 13.3 N, and the tackiness was "1: None".

Next, the same procedures as in Example 1 were carried out except using (L7) as the film-coating liquid, to give film-coated granules (F8). The resulting film-coated granules (F8) had the film-coated amount of 20% by mass (based on elementary granules (G1)), and the average particle diameter of 273 μm (the film thickness was about 17.5 μm). The collection ratio was 99.7%, and the agglomeration ratio was 4.8% (355 μm or more). The dissolution rates of riboflavin were 82.5% at 2 hours, 96.6% at 4 hours, 100% at 6 hours, 100% at 8 hours, and 100% at 10 hours.

Figure 8:
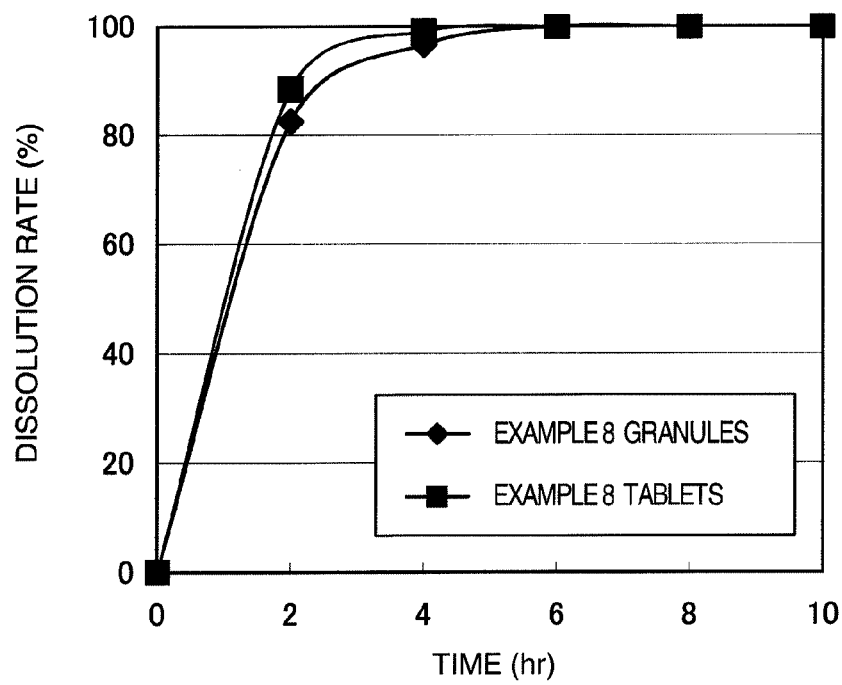

Lastly, the same procedures as in Example 1 were carried out except using (F8) as the film-coated granules, to give tablets comprising the film-coated granules in 50% by mass. The resulting tablet had the hardness of 70 N, the disintegration time of 79 s, and the tablet weight variation of 0.9%. The dissolution rates of riboflavin were 88.4% at 2 hours, 99.0% at 4 hours, 100% at 6 hours, 100% at 8 hours, and 100% at 10 hours. Namely, the amount of water-soluble substance added correlated with the dissolution rate of the drug, and sustained-release film-coated granules-containing tablets which were excellent in hardness and disintegrating property with less weight variation and had nearly-unchanged drug dissolution patterns as compared to the film-coated granules before tableting could be obtained. The drug dissolution pattern is shown in FIG. 8.

Comparative Example 1

The same procedures as in Example 1 were carried out, to prepare a film-coating liquid (solid content concentration of 17% by mass) (L8) with the solid content mass ratio of the formulation components of a:b:c:d=72.5:7.5:20:0 (=100:10.7:27.6:0). The cast film had the tensile elongation of 450% and the tensile strength of 24 N, and the tackiness was "3: Weak".

Next, the same procedures as in Example 1 were carried out except using (L8) as the film-coating liquid, to give film-coated granules (F9). The resulting film-coated granules (F9) had the film-coated amount of 20% by mass (based on elementary granules (G1)), and the average particle diameter of 271 μm (the film thickness was about 16.5 μm). The collection ratio was 83.5%, and the agglomeration ratio was 26.5% (355 μm or more). Namely, since (L8) did not comprise titanium oxide, the film had high tackiness. Therefore, adhesion to the inner side of the coating apparatus and agglomerated particles were much generated.

Comparative Example 2

The same procedures as in Example 1 were carried out, to prepare a film-coating liquid (solid content concentration of 17% by mass) (L9) with the solid content mass ratio of the formulation components of a:b:c:d=50:27.5:20:2.5 (=100:55:40:5). The cast film had the tensile elongation of 82% and the tensile strength of 7.5 N, and the tackiness was "1: None".

Next, the same procedures as in Example 1 were carried out except using (L9) as the film-coating liquid, to give film-coated granules (F10). The resulting film-coated granules (F10) had the film-coated amount of 20% by mass (based on elementary granules (G1)), and the average particle diameter of 270 μm (the film thickness was about 16.0 μm). The collection ratio was 99.6%, and the agglomeration ratio was 0.8% (355 μm or more). The dissolution rates of riboflavin were 45.0% at 2 hours, 69.1% at 4 hours, 83.5% at 6 hours, 93.8% at 8 hours, and 98.6% at 10 hours.

Figure 9:
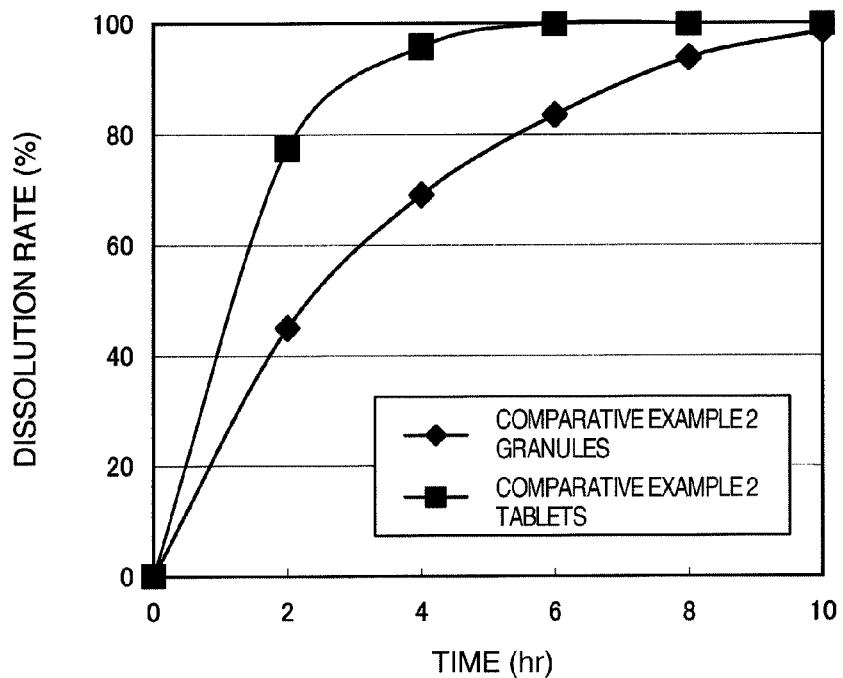

Lastly, the same procedures as in Example 1 were carried out except using (F10) as the film-coated granules, to give tablets comprising the film-coated granules in 50% by mass. The resulting tablet had the hardness of 40 N, the disintegration time of 75 s, and the tablet weight variation of 0.6%. The dissolution rates of riboflavin were 77.4% at 2 hours, 95.8% at 4 hours, 100% at 6 hours, 100% at 8 hours, and 100% at 10 hours. The drug dissolution pattern is shown in FIG. 9.

Since the amount of (b) ethyl cellulose added was high, tackiness of the film was low, and therefore, the yield of the film coating was very good. However, on the other hand, since the tensile elongation and tensile strength of the film were not enough, the film was damaged by stress upon tableting, and sustained-release property was impaired.

Comparative Example 3

The same procedures as in Example 1 were carried out, to prepare a film-coating liquid (solid content concentration of 17% by mass) (L10) with the solid content mass ratio of the formulation components of a:b:c:d=59.8:6.4:31.6:2.2 (=100:10.7:53:3.6). The cast film had the tensile elongation of 135% and the tensile strength of 10.2 N, and the tackiness was "1: None".

Next, the same procedures as in Example 1 were carried out except using (L10) as the film-coating liquid, to give film-coated granules (F11). The resulting film-coated granules (F11) had the film-coated amount of 20% by mass (based on elementary granules (G1)), and the average particle diameter of 275 μm (the film thickness was about 18.5 μm). The collection ratio was 99.5%, and the agglomeration ratio was 6.7% (355 μm or more). The dissolution rates of riboflavin were 65.3% at 2 hours, 90.3% at 4 hours, 100% at 6 hours, 100% at 8 hours, and 100% at 10 hours.

Figure 10:
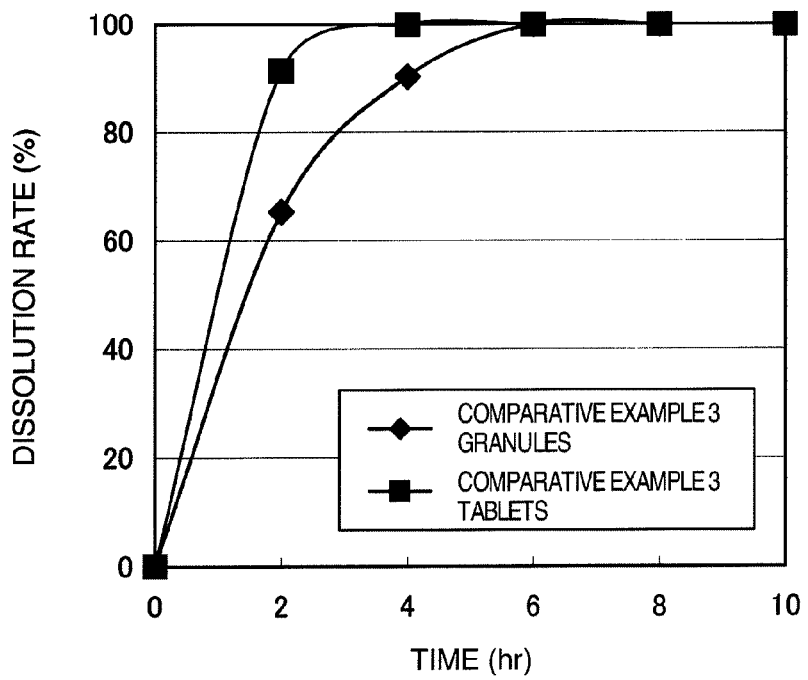

Lastly, the same procedures as in Example 1 were carried out except using (F11) as the film-coated granules, to give tablets comprising the film-coated granules in 50% by mass. The resulting tablet had the hardness of 40 N, the disintegration time of 75 s, and the tablet weight variation of 0.6%. The dissolution rates of riboflavin were 91.4% at 2 hours, 100% at 4 hours, 100% at 6 hours, 100% at 8 hours, and 100% at 10 hours. The drug dissolution pattern is shown in FIG. 10.

Since the amount of (c) hypromellose TC-5(E), i.e. a water-soluble substance, added was high, the tensile elongation of the film was not enough, the film was damaged by stress upon tableting. In addition, the high dissolution rate which was hardly recognized as a dissolution characteristic feature of sustained-release property was shown.

Comparative Example 4

The same procedures as in Example 1 were carried out except using (f) talc instead of (d) titanium oxide, to prepare a film-coating liquid (solid content concentration of 17% by mass) (L11) with the solid content mass ratio of the formulation components of a:b:c:f=70:7.5:20:2.5 (=100:10.7:28.6:3.6). The cast film had the tensile elongation of 285% and the tensile strength of 12.8 N, and the tackiness was "3: Weak".

Next, the same procedures as in Example 1 were carried out except using (L11) as the film-coating liquid, to give film-coated granules (F12). The resulting film-coated granules (F12) had the film-coated amount of 20% by mass (based on elementary granules (G1)), and the average particle diameter of 276 μm (the film thickness was about 19.0 μm). The collection ratio was 87.8%, and the agglomeration ratio was 21.5% (355 μm or more). The dissolution rates of riboflavin were 55.0% at 2 hours, 86.0% at 4 hours, 96.5% at 6 hours, 100% at 8 hours, and 100% at 10 hours.

Lastly, the same procedures as in Example 1 were carried out except using (F12) as the film-coated granules, to give tablets comprising the film-coated granules in 50% by mass. The resulting tablet had the hardness of 46 N, the disintegration time of 70 s, and the tablet weight variation of 0.9%. The dissolution rates of riboflavin were 74.3% at 2 hours, 95.6% at 4 hours, 100% at 6 hours, 100% at 8 hours, and 100% at 10 hours.

By using (f) talc instead of (d) titanium oxide, tackiness could not be reduced, agglomeration was much generated, and the film layer became inhomogeneous, and thus the film was damaged by stress upon tableting.

In addition, the compositions and the like of the above film-coating liquids are shown in Table 1.

TABLE 1

| | (a): NE30D | (b): ECD | (c): Water-Soluble Additive for Pharmaceuticals | (d): TiO2 | Average Diameter of Core Particles | Collection Ratio (%) | Agglomeration Ratio (%) | Elongation (%) | Strength (N) | Dissolution of Granules (2, 4, 6, 8, 10 hr) Dissolution of Tablet (2, 4, 6, 8, 10 hr) | | | | |
|---|---|---|---|---|---|---|---|---|---|---|---|---|---|---|
| Example 1 | 100 | 10.7 | 28.6 | 3.6 | 237 μm (355 μm or less) | 99.9 | 5.7 | 396 | 19.8 | 41.0 | 64.4 | 78.5 | 87.0 | 92.0 |
| | | | | | | | | | | 46.2 | 69.5 | 84.1 | 91.6 | 95.5 |
| Example 2 | 100 | 10.7 | 28.6 | 0.7 | | 90.8 | 7.2 | 435 | 22.5 | 41.5 | 65.2 | 79.5 | 88.5 | 93.0 |
| | | | | | | | | | | 47.2 | 70.7 | 85.7 | 92.6 | 96.8 |
| Example 3 | 100* | 20 | 24.6 | 9.2 | | 98.8 | 4.3 | 540 | 12.5 | 45.6 | 60.9 | 73.4 | 80.7 | 84.9 |
| | | | | | | | | | | 47.1 | 62.3 | 76.0 | 84.7 | 89.6 |
| Example 4 | 100 | 10.7 | 28.6 | 3.6 | 395 μm (500 μm or less) | 99.6 | 4.3 | 396 | 19.8 | 27.1 | 49.8 | 65.0 | 74.8 | 81.2 |
| | | | | | | | | | | 35.1 | 55.8 | 70.8 | 81.7 | 86.6 |
| Example 5 | 100 | | 28.6 | 0.8 | 237 μm (355 μm or less) | 98.5 | 3.8 | 198 | 12.5 | 47.6 | 69.7 | 85.3 | 92.3 | 96.7 |
| | | | | | | | | | | 48.9 | 72.3 | 88.8 | 95.4 | 98.8 |
| Example 6 | 100 | 7 | 28.6 | 9.5 | | 91.6 | 6 | 580 | 18.9 | 41.2 | 56.6 | 70.1 | 77.6 | 83.3 |
| | | | | | | | | | | 43.7 | 58.9 | 73.3 | 81.0 | 86.8 |
| Example 7 | 100 | 10.7 | 28.6 | 6.5 | | 99.9 | 4.1 | 235 | 12.1 | 39.2 | 63.5 | 76.5 | 84.9 | 90.2 |
| | | | | | | | | | | 45.4 | 67.3 | 83.4 | 89.7 | 93.2 |
| Example 8 | 100 | 10.7 | 45 | 3.6 | | 99.7 | 4.8 | 278 | 13.3 | 82.5 | 96.6 | 100.0 | 100.0 | 100.0 |
| | | | | | | | | | | 88.4 | 99.0 | 100.0 | 100.0 | 100.0 |
| Comparative Example 1 | 100 | 10.7 | 27.6 | 0 | 237 μm (355 μm or less) | 83.5 | 26.5 | 450 | 24 | No Dissolution | | | | |
| Comparative Example 2 | 100 | 55 | 40 | 5 | | 99.6 | 0.8 | 82 | 7.5 | 45.0 | 69.1 | 83.5 | 93.8 | 98.6 |
| | | | | | | | | | | 77.4 | 95.8 | 100.0 | 100.0 | 100.0 |
| Comparative Example 3 | 100 | 10.7 | 53 | 3.6 | | 99.5 | 6.7 | 135 | 10.2 | 65.3 | 90.3 | 100.0 | 100.0 | 100.0 |
| | | | | | | | | | | 91.4 | 100.0 | 100.0 | 100.0 | 100.0 |
| Comparative Example 4 | 100 | 10.7 | 28.6 | 3.6** | | 87.8 | 21.5 | 285 | 12.8 | 55.0 | 86.0 | 96.5 | 100.0 | 100.0 |
| | | | | | | | | | | 74.3 | 95.6 | 100.0 | 100.0 | 100.0 |

*Using vinylpolymer as component (a)
**Using talc as component (d)

INDUSTRIAL APPLICABILITY

The present invention can be suitably used in the field of the production of a pharmaceutical drug-containing sustained-release preparation.

The invention claimed is:

1. Film-coated granules comprising elementary granules of an average particle diameter of 300 μm or less comprising crystalline cellulose spherical core particles and a drug, and a single film layer that coats the elementary granules formed with an aqueous composition comprising (a) an ethyl acrylate and methyl methacrylate copolymer or a plasticized vinyl acetate polymer, (b) an ethyl cellulose, (c) a water-soluble additive for pharmaceutical products, (d) titanium oxide and (e) water, wherein the solid content mass ratio among the components (a), (b), (c) and (d), a:b:c:d, is 100:(5-50):(1-50):(0.5-10), and the solid content concentration of the aqueous composition is 0.5% to 40% by mass.

2. The film coated granules according to claim 1, wherein the film layer has a tensile elongation of 150% or more and a tensile strength of 9 N or more.

3. The film coated granules according to claim 1, wherein the water-soluble additive for pharmaceutical products is at least one selected from the group consisting of hydroxypropylcellulose, hydroxypropyl methylcellulose, polyvinylpyrrolidone, lactose, sucrose, mannitol, trehalose, and sorbitol.

4. A tablet comprising film-coated granules according to claim 1.

* * * * *